United States Patent
Pacetti

(10) Patent No.: US 7,673,379 B1
(45) Date of Patent: Mar. 9, 2010

(54) METHOD OF PRODUCING A STENT-BALLOON ASSEMBLY

(75) Inventor: Stephen Dirk Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 314 days.

(21) Appl. No.: 11/801,955

(22) Filed: May 11, 2007

(51) Int. Cl.
  *B23P 11/00* (2006.01)
  *B23P 25/00* (2006.01)
  *A61F 2/82* (2006.01)

(52) U.S. Cl. .............. 29/447; 29/458; 29/515; 29/516; 427/2.24; 623/1.46

(58) Field of Classification Search .............. 29/405, 29/447, 458, 515, 516, 283.5; 427/2.1, 2.24; 623/1.46
See application file for complete search history.

(56) References Cited

U.S. PATENT DOCUMENTS

| 7,306,625 B1 * | 12/2007 | Stratford et al. ............ 623/1.46 |
| 2004/0039437 A1 * | 2/2004 | Sparer et al. ................ 623/1.15 |
| 2006/0196073 A1 * | 9/2006 | Parker ........................... 34/62 |
| 2006/0287702 A1 * | 12/2006 | Sundar ...................... 623/1.11 |

* cited by examiner

*Primary Examiner*—Jermie E Cozart
(74) *Attorney, Agent, or Firm*—Squire, Sanders & Dempsey L.L.P.

(57) ABSTRACT

A method of producing a stent-balloon assembly is disclosed which includes providing a stent having a polymeric component; exposing the stent to a relative humidity of 20% to 100%; and crimping the stent on a balloon of a catheter assembly. The polymeric component could be at least part of the material from which the stent is made or could be a constituent of a coating for the stent, such as a drug delivery coating. In lieu of or in addition to the application of humidity, a plasticizing agent can be applied to the polymeric component. A crimping device is also disclosed which allows the stent to be exposed to humidity during the crimping process.

14 Claims, 1 Drawing Sheet

METHOD OF PRODUCING A STENT-BALLOON ASSEMBLY

FIELD OF INVENTION

This invention is directed to a process for crimping polymeric stents or polymeric or polymer coated stents on balloon catheters. More particularly, the invention is directed at the use of humidity or a plasticizing agent during the crimping process. The invention is also directed to novel crimping devices capable of performing the methods of the present invention.

BACKGROUND

Percutaneous transluminal coronary angioplasty (PTCA) is a procedure for treating heart disease. A surgeon introduces a catheter assembly having a balloon portion percutaneously into the cardiovascular system of a patient via the brachial or femoral artery. The surgeon advances the catheter assembly through the coronary vasculature until the balloon portion crosses the occlusive lesion. Once in position, the surgeon inflates the balloon to radially compress the atherosclerotic plaque of the lesion and remodel the vessel wall. The surgeon then deflates the balloon to remove the catheter.

An advance on PTCA involved using an intravascular stent. Mechanically, stents act as scaffoldings, physically holding open and, if desired, expanding the vessel wall. Typically, stents compress for insertion through small vessels and then expand to a larger diameter once in position. U.S. Pat. No. 4,733,665, issued to Palmaz; U.S. Pat. No. 4,800,882, issued to Gianturco; and U.S. Pat. No. 4,886,062, issued to Wiktor disclose examples of PTCA stents. One example of a stent 2 which includes struts 4 is illustrated in FIG. 1. Stents have tubular bodies with a variety of unique strut patterns and strut geometrical configurations, sometimes with spacing or gaps between the struts.

Stents can radially self-expand off of the delivery implement on which they are positioned, or crimped, or can expand by the application of a force by the delivery implement on which the stents are crimped. Stent crimping is a critical step in manufacturing this equipment in that stent retention during delivery and implantation depends on it. Generally, stent crimping is the act of affixing the stent to the delivery catheter or delivery balloon so that it remains secured, positioned or affixed to the catheter or balloon until the physician desires to deliver the stent at the treatment site. Good stent retention is critical to a safe stent implantation procedure. With earlier generation stent systems, stents could become dislodged or fall off the system within the patient's vasculature during delivery. In other instances, the stent delivery system were not able to reach the targeted lesion. When this occurs, the delivery system is withdrawn back into the guiding catheter, and the entire system withdrawn from the patient. It has happened that the stent is stripped off of the catheter when it is withdrawn into the guiding catheter. This is particularly hazardous as it places the loose stent in the coronary ostium where any complication could affect that entire coronary artery. In order to meet the simultaneous requirements of low profile, and good stent retention with no damage to the balloon, current stent crimping technology is sophisticated. A short time ago, one process used a roll crimper. This damaged many polymer coatings due to its inherent shearing action. Next came the collet crimper; in it, metal jaws are mounted into what is essentially a drill chuck. The jaws move in a purely radial direction. This movement was not expected to shear the coating, because it applied forces only normal to the stent surface. But some stent geometries require that stent struts scissor together during crimping. In those geometries, even if the crimper imposes only normal forces, the scissor action of the stent struts imparts shear. Finally, the iris or sliding-wedge crimper was developed which imparts mostly normal forces with some amount of tangential shear.

To use a roll crimper, first the stent is slid loosely onto the balloon portion of the catheter. This assembly is placed between the plates of the roll crimper. With an automated roll crimper, the plates come together and apply a specified amount of force. They then move back and forth a set distance in a direction that is perpendicular to the catheter. The catheter rolls back and forth under this motion, and the diameter of the stent is reduced. The process can be broken down into more than one step, each with its own level of force, translational distance, and number of cycles. With regard to a polymer stent or drug delivery coated stent, this process imparts a great deal of shear to the stent in a direction perpendicular to the catheter or catheter wall. Furthermore, as the stent is crimped, there is additional relative motion between the stent surface and the crimping plates. As a result, this crimping process tends to damage the stent or the coating.

The collet crimper is equally conceptually simple. A standard drill-chuck collet is equipped with several pie-piece-shaped jaws. These jaws move in a radial direction as an outer ring is turned. To use this crimper, a stent is loosely placed onto the balloon portion of a catheter and inserted in the center space between the jaws. Turning the outer ring causes the jaws to move inward. An issue with this device is determining or designing the crimping endpoint. One scheme is to engineer the jaws so that when they completely close, they touch and a center hole of a known diameter remains. Using this approach, turning the collet onto the collet stops crimps the stent to the known outer diameter. While this seems ideal, it can lead to problems. Stent struts have a tolerance on their thickness. Additionally, the process of folding non-compliant balloons is not exactly reproducible. Consequently, the collet crimper exerts a different amount of force on each stent in order to achieve the same final dimension. Unless this force, and the final crimped diameter, is carefully chosen, the variability of the stent and balloon dimensions can yield stent, coating, or balloon damage.

Furthermore, although the collet jaws move in a radial direction, they move closer together as they crimp. This action, combined with the scissoring motion of the struts, imparts tangential shear on a polymer stent or a coating that can also lead to damage. Lastly, the actual contact surfaces of the collet crimper are the jaw tips. These surfaces are quite small, and only form a cylindrical surface at the final point of crimping. Before that point, the load being applied to the stent surface is discontinuous.

In the sliding wedge or iris crimper, adjacent pie-piece-shaped sections move inward and twist, much like the leaves in a camera aperture. This crimper can be engineered to have two different types of endpoints. It can stop at a final diameter, or it can apply a fixed force and allow the final diameter to float. From the discussion on the collet crimper, there are advantages in applying a fixed level of force as variabilities in strut and balloon dimension will not change the crimping force. The sliding wedges impart primarily normal forces, which are the least damaging to stent coatings. As the wedges slide over each other, they impart some tangential force. But the shear damage is frequently equal to or less than that of the collet crimper. Lastly, the sliding wedge crimper presents a nearly cylindrical inner surface to the stent, even as it crimps. This means the crimping loads are distributed over the entire outer surface of the stent.

All current stent crimping methods were developed for all-metal stents. Stent metals, such as stainless steel, are durable and can take abuse. When crimping was too severe, it usually damaged the underlying balloon, not the stent. But polymeric stents and polymeric coatings present different challenges.

Moreover, as part of polymeric stent manufacture, brittle polymeric material is laser cut. The polymer's brittle nature and the stress induced by laser cutting can cause stress cracking in the polymeric stent during the crimping process.

In the drug eluting or delivery stent arena, drugs are commonly placed or coated on the stent in combination with a polymer, or mixed into the polymer body for polymeric stents. This placement typically coats all stent surfaces or causes the drug to be distributed throughout the polymeric stent. Then the stent is crimped onto the catheter. In general, polymer coatings are softer, weaker, and less durable than the underlying stent material. Upon crimping, for example with a sliding wedge crimper, and following crimp protocols for the particular stent, coating damage is frequently seen. For polymers that are brittle or hard, crimping process can crack the stent coating or the polymeric stent strut.

Grip is a process conducted after crimping to further increase stent retention. An outer sleeve restrains the crimped stent. Simultaneously, pressure and heat are applied to the stent-balloon section. Under this action, the balloon material deforms slightly, moving in between the struts. In a wet expansion test, the final stent-on-catheter assembly is immersed in deionized water at 37° C. for 30 seconds. Then the balloon is inflated according to the device instructions to at least a nominal pressure (e.g., 8 atmospheres). After holding this pressure for 30 seconds, the balloon is deflated, and the stent slides off. After drying, the stent can be examined by optical microscopy or scanning electron microscopy for coating damage.

The primary purpose of the polymer in the stent coating is to contain the drug and control its release at a desired rate. Other obvious specifications for the polymer are a high level of vascular biocompatibility and the ability to flex and elongate to accommodate stent expansion without cracking or peeling. Meeting all of these objectives, while also possessing a high level of toughness and strength to withstand conventional crimping process, can be challenging.

A crimping device and process that minimizes damage to the polymer coatings of stents is needed. Moreover, a crimping process that minimizes internal stress or strain in the polymeric substrate of a polymeric stent is also needed.

SUMMARY

The current invention is related to devices and methods for making medical devices such as implantable medical devices, including stents. These medical devices can comprise portions with coatings. In some embodiments, the coating comprises a polymer, polymer combination, drug(s), or combination of polymer(s) and drug(s). In some embodiments, the device itself can be made in full or in part from a polymer or polymer combination. The piece comprising the coating or made from the polymer is crimped onto another part of the medical device or onto a separate medical device, such as a delivery device or a balloon of a catheter assembly. In some embodiments, crimping is done at a high and controlled humidity. The stent, with or without a coating, can be exposed to humidity immediately followed by the crimping process. The stent or coating can be exposed to humidity and the humidity maintained at least partially during the crimping process or throughout the duration of the crimping process. In some embodiments, the stent or coating can be exposed to the humidity during the crimping process and if desired the humidity can be maintained or a level of humidity can last during at least a part of the crimping process. In some embodiments, the relative humidity can be adjusted during the crimping process. In some embodiments, high humidity should exist at least until the stent is considered crimped and compressed on the balloon such as for example when the crimping apparatus has closed on the stent (e.g., crimping jaws or rollers have reduced the diameter of the stent to the desired crimped diameter). High humidity can exist or alternatively can be terminated when the crimping apparatus opens back up after securing the stent on the balloon, such as when crimping jaws or rollers are released and retracted off the stent. High humidity can be defined as at least 20% to 100% relative humidity at temperature of 25° C. In some embodiments, the relative humidity (at 25° C.) can be at least 25%, 30%, 35%, 40%, 45%, 50%, 55%, 60%, 65%, 70%, 75%, 80%, 85%, 90%, 95%, 100% or any range between any of these disclosed percentages (e.g., 20% to 60%; 30% to 35%; 50% to 95%, etc.). Following the crimping process, moisture can be allowed to evaporate or can be removed by force, such as by exposure to high temperatures or blowing gas, such as an inert gas, onto the stent. The gas can be at an elevated temperature.

In some embodiments, the stent or coating can be exposed to a plasticizing agent such as a plasticizing solvent or fluid followed by the crimping process. The plasticizing agent should remain on or have migrated within the stent body or coating for the crimping process. In some embodiments, the agent can be introduced to the stent or the coating during the crimping process and should remain on or within the stent or coating during at least a part of the crimping process or during the entire duration of the crimping process.

In accordance with another aspect of the invention, a stent crimping device is provided that includes a crimping chamber or section in which the stent can be positioned and a component or introducing water vapor, moisture (purified water or buffered saline solution), or a plasticizing agent into the crimping chamber or section.

In some embodiments, the temperature of the plasticizing fluid or solvent should be at non-ambient temperatures.

The methods and devices of the present invention can be used on a variety of polymeric materials including those characterized as having a glass transition temperature (Tg) above ambient temperature. Preferably, the polymer has a Tg, in a dry state, prior to exposure to humidity, above: 30° C., 40° C., 50° C., 60° C., 70° C., and 80° C. More preferably, the polymer can have a dry state Tg above 90° C.

In some embodiments, the devices and methods of the present invention are preferably used with polymers having greater than a 60 shore D hardness. In some embodiments, shore D hardness of the polymer can be greater than 65, 70, 75, 80, 85, 90, and 95.

Some embodiments operate on drug-containing pieces. In some of these embodiments, the drugs are selected from the following types: antiproliferative, antineoplastic, antiinflammatory, antiplatelet, anticoagulant, antifibrin, antithrombin, antimitotic, antibiotic, antioxidants, or their combinations.

In some embodiments, high humidity is selected from a group that specifically excludes any one or any combination of the humidity ranges described herein. In some embodiments, the selection of the relative humidity is based on minimizing stent or coating damage, including cracking of the polymer, as well as deformation- and delamination-based failure during crimping.

DETAILED DESCRIPTION

Figure 1:
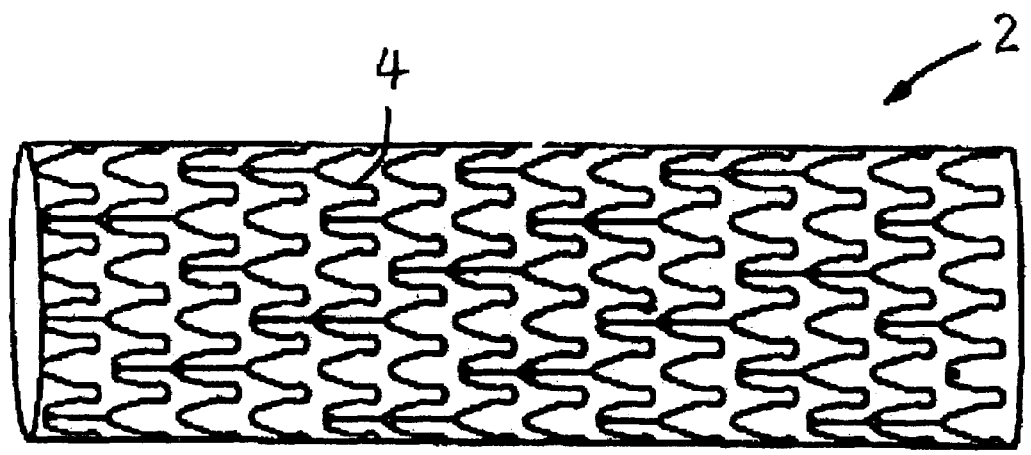
FIG. 1 shows a conventional stent.

The current invention is related to devices and method of making medical devices such as implantable medical devices, including stents. A stent can be self-expandable or balloon expandable. The stent can be a stent-graft. These devices can comprise portions with coatings or can be fully coated. In some embodiments, the coating comprises a polymer, polymer combination, drug(s), or combination of polymer(s) and drug(s). The coating can be of a single layer construct or multiple layers. The coating can be deposited over a metallic substrate. Coatings can be produced by dissolving a polymer and optionally a drug in a solvent, and applying (e.g., spraying) this composition to the stent. Once the solvent is removed, a polymeric coating with or without a drug can remain on the stent. In some embodiments, the device itself can be made in full or in part from a polymer or polymer combination. For example, the device can be a bioabsorbable polymeric stent, with or without a coating. In other words, the struts of the stent which can function to uphold luminal patentcy can be made from a bioabsorbable polymer. A coated or coat-less piece is crimped onto another part of the device or onto a separate medical device, such as a delivery device or a balloon of a catheter assembly. Preferably, the medical device is a polymeric stent, a metallic stent having a polymeric coating, or a polymeric stent having a polymeric coating that is crimped on a balloon of a catheter assembly.

In some embodiments, crimping is done at a high and controlled humidity. Crimping is defined as the process of compressing, securing, collapsing, loading or mounting the medical device, e.g., stent, on a delivery system, e.g., balloon of a catheter such that the stent has no to little relative movement with respect to the balloon during the delivery process and is fixedly carried by the balloon until purposeful disengaged from the balloon upon inflation of the balloon by a medical operator. The crimper can include jaws, rollers, belts, sliding plates, bladders or similar actuating mechanisms for performing the crimping function. The crimping process generally includes the steps of inserting the stent into a crimping apparatus followed by crimper engagement with the stent. The engagement includes application of pressure or force to the stent until the stent is reduced to a designated diameter. The force applied can be uniform or vary through the reduction of stent diameter. The force can also vary along the length of the stent. The force can be maintained for duration of time (e.g., seconds to minutes) until the stent is adequately crimped on the balloon. The crimping device then is disengaged from the stent and the stent can be removed from the apparatus. Examples of crimping device used in the art include those disclosed by U.S. Pat. Nos. 6,968,607; 6,925,847; 6,920,674; 6,108,886; 6,092,273; 6,082,990; 6,074,381; 6,063,102; 6,769,161; 6,726,713; and 6,640,412. The crimping can be performed in a closed chamber for creation and maintenance of the humidity. In some embodiments, as illustrated in FIG. 2, the crimping device can include a receiving chamber, in which the stent is disposed, for allowed the stent to be exposed to high relative humidity.

Figure 2:
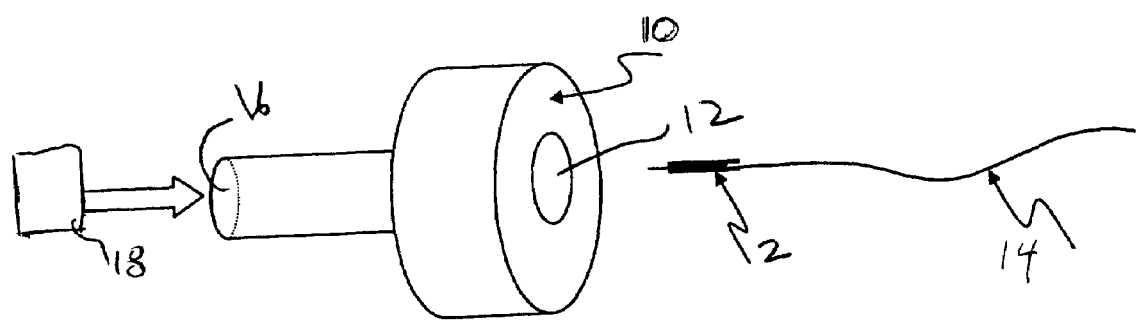
FIG. 2 shows a crimping apparatus in accordance with one embodiment of the present invention.

Referring to FIG. 2, an embodiment of a crimping device 10 is illustrated having a work space or chamber 12 for receiving a stent 2 positioned over a balloon of a catheter 14. The stent 2 is positioned on the balloon and feed into the work space 12. The work spaces closes, applying a force to the stent 2, reducing the stent diameter, and crimping the stent 2 on the balloon. The crimping apparatus 10 has been modified to include an inlet 16. The inlet 16 allows the work space 12 to be in fluid communication with a humidity source 18 to expose the stent to vapor or moisture including purified water or buffered saline solution.

The coat-less stent or coated stent can be exposed to humidity followed immediately by introducing the stent into a crimping apparatus. In only words, the stent is first disposed within a humidity chamber for 5 minutes to 24 hours, for example. The stent is then removed from the humidity chamber and immediately placed within the crimping device. In some embodiments, the crimping can be conducted in the humidity chamber after the stent has been exposed to a high relative humidity for a selected period of time. The stent or coating can be exposed to humidity and the humidity maintained at least partially during the crimping process or throughout the duration of the crimping process. It is preferably that the humidity be maintained at least until the crimping device compresses the stent onto the balloon. Maintaining the relative humidity can be defined as +/−1%, +/−2%, +/−5% or +/−10% deviation.

As for the device of FIG. 2, for example, the stent 2 is introduced into the workspace 12 and subjected to high humidity for duration of time. Moisture or water vapor is introduced into the work space 12 via the inlet or conduit 16 from the humidity source 18. Once the coat-less stent or coating of the stent has absorbed a sufficient amount of moisture, the work-space encloses on the stent, crimping the stent on the balloon. The application of humidity can be until the crimping device has engaged the stent. Alternatively, the application of humidity can be terminated anytime during the engagement of the crimper with the stent or until termination of the engagement with the stent. Yet, alternatively, application of humidity can continue for sometime past the disengagement of the crimper with the stent. Such time frames for application of humidity are applicable to all embodiments of the present invention.

In some embodiments, the coat-less stent or coated stent can be exposed to the humidity during the crimping process and if desired the humidity can be maintained during at least a part of the crimping process. In some embodiments, the relative humidity can be adjusted during the crimping process, either increased or decreased. For example, the amount of water vapor or moisture introduced into the workspace 12 can be reduced as the workspace 12 encloses on the stent. Reduction can be incremental or in a step-wise fashion. In some embodiments, high humidity should exist at least until the stent is considered crimped and compressed on the balloon (e.g., crimping jaws or rollers have reduced the diameter of the stent to the desired crimped diameter).

In some embodiments humidified gas or air can be applied such as through inlet 16 such that the temperature of the applied air or gas may be different from ambient temperature or the clean room temperature. In some embodiments the temperature can be above 25 deg. C. The upper limit can be below 300 deg. C., 200 deg. C. or alternatively below 100 deg. C. In some embodiments, the temperature can be the same as ambient or even below ambient.

High humidity can exist or the desired level of high humidity can be maintained while the crimping apparatus opens back up after securing the stent on the balloon such as when crimping jaws or rollers are released and retracted off the stent.

High humidity can be defined as higher than ambient humidity or humidity in the clean room where the stent crimping process is performed. In some embodiments, high humidity is least 20% to 100% relative humidity at temperature of 25° C. In some embodiments, the relative humidity (at 25° C. or at the temperature of the clean room in which the procedure in conducted) can be at least 25%, 30%, 35%, 40%, 45%, 50%, 55%, 60%, 65%, 70%, 75%, 80%, 85%, 90%, 95%, 100% or any range between any of these disclosed percentages (e.g., 20% to 60%; 30% to 35%; 50% to 95%, etc.).

Following the crimping process, moisture can be allowed to evaporate or can be removed by force, such as exposure to high temperatures or blowing a gas, such as inert gas, on the stent. The gas can be at an elevated temperature. The selection of the relative humidity can be based on minimizing stent or coating damage, including cracking of the polymer, as well as deformation- and delamination-based failure during crimping.

In some embodiments, the high humidity should cause the coat-less stent or the stent coating to absorb greater than 0 (e.g., 0.1) and less than 40% by weight moisture. It is preferable for the stent or coating to absorb greater than 0 and less than 40% by weight moisture prior to the application of force to the stent by the crimper. This moisture level should be maintained during the crimping process or at least until the point where the crimper disengages from the stent. In some embodiments, this moisture level can be carried out sometime past the release of the stent by the crimper. In some embodiments, the moisture level can be 10% to 30% by weight, more narrowly 15% to 25% by weight. The moisture level can also be adjusted, either increased or decreased during the crimping process. For example, as the crimper is applying pressure on the stent, the moisture level can be deceased incrementally by application of heat.

In some embodiments, the high humidity should cause the Tg of the polymer component of the stent to decrease. The Tg can decrease by more the 1%, 2%, 5%, 10%, 15%, 20%, 30%, 40%, 50%, 60% or alternatively 70%. In some embodiments, it should not be reduced by more than 90%, 80%, 70%, 60%, 50%, 40%, 30%, 25%, 20%, 10%, or 5%. In some embodiments, the Tg of the polymeric component is reduced between 10% and 90%, between 20% and 80%, between 30% and 70%, or alternatively between 40% and 60%. Preferably, the Tg is reduced between 5% to 50% or 10% to 50%. All temperature values are measured in Celsius.

In lieu of, or in addition to, the humidity treatment, the polymeric component of the stent can be exposed to a plasticizing agent prior to introducing the stent into the crimping apparatus. The plasticizing agent can be added to the polymeric component in a dry state. For example, the plasticizing agent can be added to a coating that has less than 2% by weight or more narrowly less than 1% by weight residual solvent that was used to manufacture the coating. In some embodiments, the coating should have less than 0.1% residual coating solvent or should be completely (0% by weight) solvent free when the plasticizing agent is applied. The plasticizing agent can reduce the glass transition temperature of the polymer at the same levels described above. The plasticizing agent can be a gas, fluid, a solvent, or a liquid or gas carrier including the agent. In some embodiment, the plasticizing agent can be a gaseous element or compound. The exposure can be by spraying the stent or immersing the stent in a liquid agent or a liquid carrying the agent. At least a majority (>50% of what was applied) of the agent should remain on or have migrated within the stent body or coating during at least a part of the crimping process or during the entire duration of the crimping process. Preferably, at least a majority of the fluid or solvent should remain up to the point where the crimper starts engaging the stent.

In some embodiments, the plasticizing agent can be introduced to the stent or the coating prior to and/or during the crimping process and should remain on or within the stent or coating during at least a part of the crimping process or during the entire duration of the crimping process. For example, referring to FIG. 2, a plasticizing agent can be introduced into the inlet 16 for contacting the stent 2 in the workspace 12.

Subsequent to the crimping process, the moisture or plasticizing agent can be removed from the stent body or the coating on the stent. The removal can be by evaporation at room temperature or can be induced by heating. The stent can be placed in a regular oven or convection oven. Alternatively, a heated air or gas, such as an inert gas, can be directed at the stent. Preferably, the gas can be argon or nitrogen. The heating can commence as soon as the crimping device initiates disengagement from the stent. For example, heated gas having a temperature between 30° C. to 200° C. can be forced into inlet 16.

In accordance with another aspect of the invention, a stent crimping device is provided that includes a crimping chamber, workspace or section in which the stent can be positioned. The crimper can include an inlet for allowing humidity (water, water vapor or moisture, buffered saline solution, etc), or a plasticizing agent (liquid agent, liquid carrier including the agent, plasticizing gas) into the crimping workspace.

In some embodiments, the temperature of the plasticizing agent when exposed to the stent can be at non-ambient temperatures, such at between 30° C. to 100° C.

The methods and devices of the present invention can be used on a variety of polymeric materials including those characterized as having a Tg above ambient temperature. Preferably, the polymer has a Tg in a dry state, prior to exposure to the humidity, above: 30° C., 40° C., 50° C., 60° C., 70° C., and 80° C. More preferably, the methods and devices of the invention are used with polymers having a dry state Tg above 90° C.

In some embodiments, the devices and methods of the present invention are preferably used with polymers having a hardness greater than 60 shore D (in a dry state or prior to treatment). In some embodiments, the shore D hardness of the polymer can be greater than 40, 45, 50, 55, 60, 65, 70, 75, 80, 85, 90, and 95 (in dry state or prior to treatment). The embodiments of the present invention can be used to yield at least 50% decrease in shore hardness, alternatively, at least 40%, 30%, 25%, 20%, 15%, 10%, 5%, or 1% decrease in shore D hardness. In some embodiments, the shore D hardness should not be decreased by more than 90%, 80%, 70%, 60%, 50%, 40%, 30%, 25%, 20%, 10% or 5%. In some embodiments, it can be decreased 10% to 90%, 10% to 80%, 10% to 70%, 10% to 60%, 10% to 50%, 10% to 40%, 10% to 30%, 10% to 20%, 20% to 80%, 20% to 70%, 20% to 60%, 20% to 50%, 20% to 40%, or 20% to 30%.

Examples of plasticizing agents include solvents such as methanol, ethanol, isopropanol, n-propanol, n-butanol, acetone, 2-butanone, diethyl ether, tetrahydrofuran, dioxane acetonitrile, dimethyl formamide, dimethyl acetamide, dimethyl sulfoxide, 1-methoxy-2-propanol, methyl acetate, ethyl acetate, n-butyl acetate, methylene chloride, chloroform, toluene, pentane, hexane, cyclohexane, liquid freons, and any combination thereof.

Gaseous plasticizing agents include gaseous freons, gaseous fluorocarbons, gaseous fluorohydrocarbons, gaseous chlorofluorocarbons, gaseous chlorofluorocarbons, gaseous chlorocarbons, perfluoromethane, difluoromethane, chloromethane, methane, ethane, propane, butane, carbon dioxide, nitrous oxide, argon, neon, hydrogen sulfide, carbon monoxide, sulfur hexafluoride and any combination thereof.

Conventional plasticizers may be used such as phthalate esters, isophthalate esters, terephthalate esters, citric acid esters, fatty acids, fatty acid esters, fatty alcohols, triglycerides, diglycerides, monoglycedrides and any combination thereof. Limitations with conventional plasticizing agents can include the ability to rapidly add and remove them to the polymeric coating via a gas phase.

Lastly, for practically any polymer, a good plasticizer can be the monomer of which that polymer is composed. These are often unsaturated molecules, with some potential reactivity, so their removal after the process is desirable.

Any of the above agents can be in solid, liquid, gas or vapor form.

In some embodiments, the intent of the invention, for example reduction is glass transition temperature or shore harness can be achieved by exposure, at any of the previously disclosed time periods, of the polymeric component (e.g., coating on a balloon expandable stent) to a process selected from a group consisting of exposure to vapor, exposure to moisture, exposure to a gas, exposure to a plasticizing agent, exposure to a solvent vapor, exposure to polymer monomer vapor, exposure to liquid solvent, exposure to liquid polymer monomer, exposure to plasticizing agent vapor, such that the vapor, gas, agent, solvent, etc. can be selected from anyone of the disclosed material.

The percentage and duration of humidity or the amount of plasticizing agent should be of a level that the material becomes ductile enough to adequately lower the brittleness of the stent or the coating of the stent. Adequate means having a value for the parameter in question such that one of ordinary skill in the art would expect the invention to function in the particular application. For example, "adequately lower the brittleness of the stent" means that the brittleness of the stent is reduced enough to such that the cracking in the stent or coating is reduced or significantly minimized (as compared to when any of the procedures of the present invention are not followed).

Polymers on crimped stents or crimped polymeric stents exhibit adhesive and cohesive failure as two main failure modes. In adhesive failure, polymer is sheared off the stent due to poor adhesion to the metal stent or between the polymer molecules in a polymeric stent. This is a failure of the polymer due to poor interaction between polymer molecules and the substrate. Since moisture and other plasticizing agents make polymeric materials softer, the methods of the present invention should assist in preventing adhesive failure. Adhesive failure is sometimes referred to as an adhesive-based failure or delamination-based failure. When a polymer exhibits adhesive failure, that polymer becomes a candidate for crimping methods of the present invention. Adhesive failure is also caused by a build-up of stress. Moisture and plasticizing agents lower the polymer's modulus and decreases the internal stress within the polymer. When stents are crimped, whether polymer coated or substantially polymeric, certain portions of the stent undergo elongation and compression. If too much elongation occurs, the polymer will crack. The ultimate elongation of polymers depends on a variety of factors, including presence of moisture or plasticizing agent. The embodiments of the present invention can increase the ultimate elongation, thereby preventing failure. If the polymer exhibits a cohesive failure due to insufficient elongation, it is also a candidate for crimping methods of the present invention.

In some embodiments, the medical devices are to be those adapted for placement in arterial, venous, neurovascular, urethral, biliary, prostate, intravascular, ureteral, bronchial, esophageal, fallopial, tracheal, laryngeal, gastrointestinal, lymphatic, eustachiaic, pancreatic, cerebral, other genitourinary, other gastrointestinal, or other respiratory lumens or passages.

In some embodiments the methods act on polymeric materials comprising ABS resins; acrylic polymers and acrylic copolymers; acrylonitrile-styrene copolymers; alkyd resins; biomolecules; cellulose ethers; celluloses; copoly(ether-esters); copolymers of polycarboxylic acids and poly-hydroxycarboxylic acids; copolymers of vinyl monomers with each other and olefins; cyanoacrylates; epoxy resins; ethylene vinyl alcohol copolymers; ethylene-methyl methacrylate copolymers; ethylene-vinyl acetate copolymers; ethylene-α-olefin copolymers; poly(amino acids); poly(anhydrides); poly(butyl methacrylates); poly(ester amides); poly(ester-urethanes); poly(ether-urethanes); poly(imino carbonates); poly(orthoesters); poly(silicone-urethanes); poly(tyrosine arylates); poly(tyrosine-derived carbonates); polyacrylates; polyacrylic acid; polyacrylic acids; polyacrylonitrile; polyacrylonitrile; polyalkylene oxalates; polyamides; polyamino acids; polyanhydrides; polycarbonates; polycarboxylic acids; polycyanoacrylates; polyesters; polyethers; poly-hydroxycarboxylic acids; polyimides; polyisobutylene and ethylene-α-olefin copolymers; polyketones; polymethacrylates; polyolefins; polyorthoesters; polyoxymethylenes; polyphosphazenes; polyphosphoesters; polyphosphoester urethanes; polyphosphoesters; polyphosphoesters-urethane; polyurethanes; polyvinyl aromatics; polyvinyl esters; polyvinyl ethers; polyvinyl ketones; polyvinylidene halides; silicones; starches; vinyl copolymers vinyl-olefin copolymers; and vinyl halide polymers and copolymers. Specific examples of useful polymers for some embodiments include the following polymers: starch, sodium alginate, rayon-triacetate, rayon, polyvinylidene fluoride, polyvinylidene chloride, polyvinyl pyrrolidone, polyvinyl methyl ether, polyvinyl chloride, polyvinyl acetate, polystyrene, polyisocyanate, polyisobutylene, polyethylene glycol, polydioxanone, polycaprolactone, polycaprolactam, KYNAR (brand poly(vinylidene fluoride) available from Atofina), polyacrylonitrile, poly(trimethylene carbonate), poly(L-lactic acid), poly(lactide-co-glycolide), poly(hydroxyvalerate), poly(hydroxybutyrate-co-valerate), poly(hydroxybutyrate-co-hydroxyvalerate), poly(hydroxybutyrate), poly(glycolide), poly(glycolic acid), poly(D,L-lactide-co-L-lactide), poly(D,L-lactide-co-glycolide), poly(D,L-lactide), poly(4-hydroxybutyrate), poly(3-hydroxybutyrate), poly(3-hydroxy valerate), Nylon 66, hyaluronic acid, fibrinogen, fibrin, elastin-collagen, collagen, cellulose propionate, cellulose nitrate, cellulose butyrate, cellulose acetate butyrate, cellulose acetate, cellulose, cellophane, carboxymethyl cellulose, or poly(2-hydroxyethyl methacrylate), Chitin, Chitosan, EVAL, poly(butyl methacrylate), poly(D,L-lactic acid), poly(D,L-lactide), poly(glycolic acid-co-trimethylene carbonate), poly(hydroxybutyrate-co-valerate), poly(hydroxyvalerate), poly (iminocarbonate), poly(lactide-co-glycolide), poly(L-lactic acid), poly(N-acetylglucosamine), poly(trimethylene carbonate), poly(vinyl chloride), poly(vinyl fluoride), poly(vinylidene chloride), poly(vinylidene fluoride), poly(vinylidene fluoride-co-chlorotrifluoroethylene), poly (vinylidene fluoride-co-hexafluoropropene), polyanhydride, polyorthoester, polyurethane, polyvinyl alcohol, polyvinyl chloride, rayon, SOLEF 21508 (formulation available from Solvay Solexis), and PEO/PLA. Some embodiments select the group of polymers to specifically exclude any one of or any combination of the polymers listed above.

In one embodiment, the methods of the invention are particularly used for PC1036 polymer or coating or stent body including this polymer. PC1036 can be used as a mixture with any of the above described polymers. PC1036 is a phosphoryl choline acrylate polymer produced by Biocompatibles (based out of the United Kingdom). PC1036 is an all-acrylate backbone, synthetic polymer, which cross-links to form a contiguous coating. PC1036 can be represented as follows:

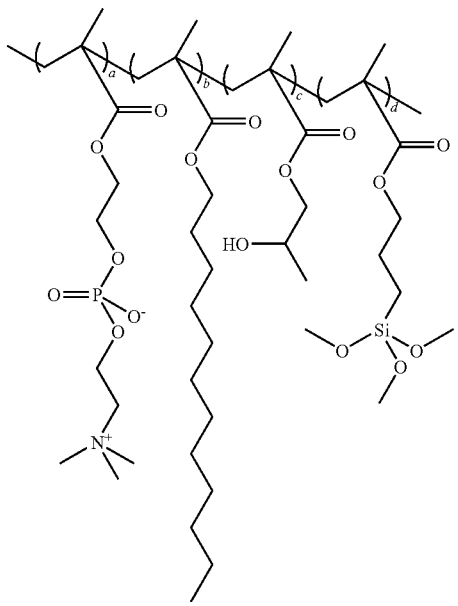

Mol%: a = 23, b = 47, c = 25, d = 5
Wt%: a = 28.8, b = 50.7, c = 15.3, d = 5.3

Scheme IA and IB are cross-linking schemes:

Scheme IA

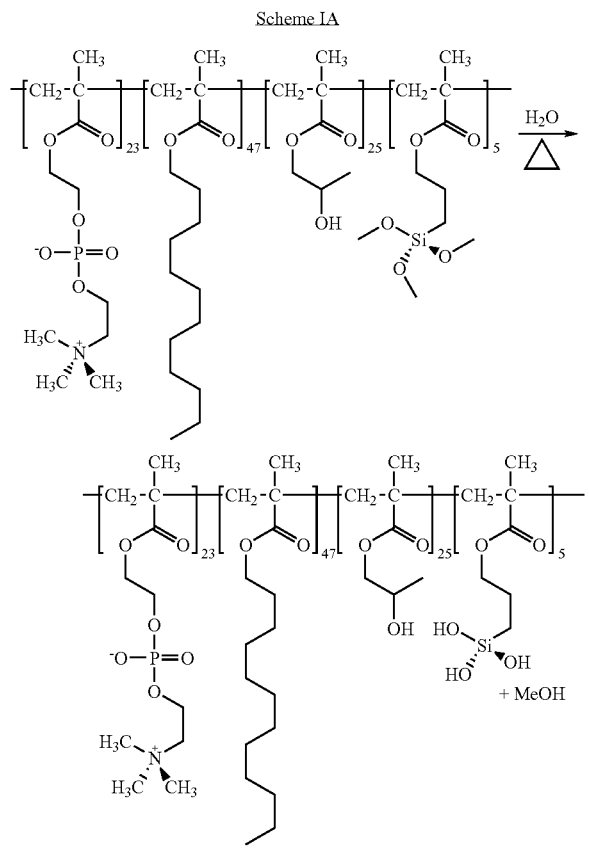

Scheme IB

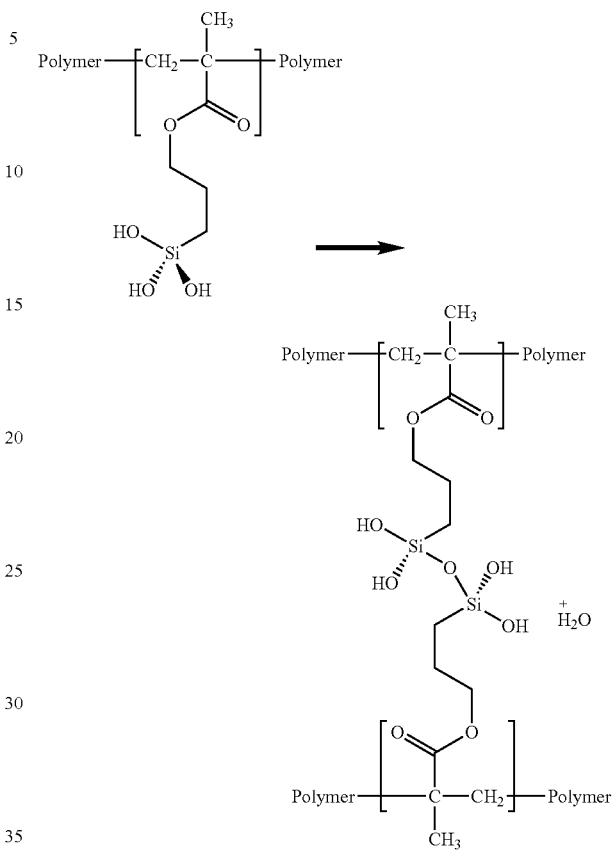

When dry, PC1036 is quite brittle with a Tg of 95° C. However, the polymer can absorb up to 30% water by weight, and becomes quite flexible.

The polymeric component for use with this invention can comprise a mixture of polymers, such as an intimate mixture of polymer molecules, or can use a combination of polymers arranged in a layered structure. The polymers used can also be chemically bonded or crosslinked.

Some embodiments add conventional drugs, such as small, hydrophobic drugs. Some embodiments graft-on conventional drugs or mix conventional drugs with the polymers. The polymers can serve as base or topcoat layers for the coating constructs.

The selected drugs can inhibit vascular, smooth muscle cell activity. More specifically, the drug activity can aim at inhibiting abnormal or inappropriate migration or proliferation of smooth muscle cells to prevent, inhibit, reduce, or treat restenosis. The drug can also include any substance capable of exerting a therapeutic or prophylactic effect. Examples of such active agents include antiproliferative, antineoplastic, antiinflammatory, antiplatelet, anticoagulant, antifibrin, antithrombin, antimitotic, antibiotic, and antioxidant substances, as well as their combinations, and any prodrugs, metabolites, analogs, congeners, derivatives, salts and their combinations.

An example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin II, actinomycin X1, and actinomycin C1.

Examples of antineoplastics include paclitaxel and docetaxel. Examples of antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ib-sen), angiotensin converting enzyme inhibitors such as CAPTOPRIL (available from Squibb), CILAZAPRIL (available from Hoffman-LaRoche), or LISINOPRIL (available from Merck & Co., Whitehouse Station, N.J.), calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck & Co.), monoclonal antibodies (such as PDGF receptors), nitroprusside, phosphodiesterase inhibitors, prostaglandin inhibitor (available from Glazo), Seramin (a PDGF antagonist), serotonin blockers, thioprotease inhibitors, triazolopyrimidine (a PDGF antagonist), and nitric oxide. Other useful drugs may include alpha-interferon, genetically engineered epithelial cells, dexamethasone, estradiol, clobetasol propionate, cisplatin, insulin sensitizers, receptor tyrosine kinase inhibitors, and carboplatin. Exposure of the composition to the drug should not adversely alter the drug's composition or characteristic. Accordingly, drug containing embodiments choose drugs that are compatible with the composition. Rapamycin is a suitable drug. Additionally, methyl rapamycin, everolimus, 40-O-(2-hydroxy)ethyl-rapamycin, 40-O-tetrazolylrapamycin (ABT-578), or 40-epi-(N-1-tetrazolyl)-rapamycin or functional analogs or structural derivatives thereof, is suitable, as well. Examples of analogs or derivatives of 40-O-(2-hydroxy)ethyl-rapamycin include, among others, 40-O-(3-hydroxy)propyl-rapamycin and 40-O-2-(2-hydroxy) ethoxyethyl-rapamycin. Those of ordinary skill in the art know of various methods and coatings for advantageously controlling the release rate of drugs, such as 40-O-(2-hydroxy)ethyl-rapamycin.

Examples of implantable devices useful in the present invention include self-expandable stents, balloon-expandable stents, and stent-grafts. The underlying structure of the device can be of virtually any design. The device can comprise a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium, and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The stent can be made from a bioabsorable polymer. Bioabsorbable is intended to include biodegradable, bioerodable and biodissolvable polymers. Of course, one of ordinary skill in the art recognizes that the invention is useful for medical devices that use a crimping step in their production.

Any of the above described procedures can be used to reduce a stent in diameter, such as a self-expanding stent, and inserting the stent in a sheath to constrain the stent. Once the stent is withdrawn out from the sheath, the stent expands to a larger diameter.

Various, specialized tests are used to assay the integrity of a drug delivery stent coating. In all of them, completed units are tested which have been though all stent-catheter assembly processes, including crimping processes. One test is inspection of the coated stents by scanning electron microscopy. This can be done on the completed units by cutting the stent-balloon section from the catheter, or the stent can be removed from the catheter by dry expansion in air or wet expansion in aqueous solution. Under SEM, the fraction of compromised coating surface area can be estimated. Compromised coating is coating that has been cracked, deformed, torn, or removed. When this fraction of surface area exceeds 5-10%, the drug-release-rate properties, and total drug content can be affected. Another measure of coating integrity, which is tied to crimping damage, is the number and size of particles shed when the stent is expanded in aqueous solution. The stent is deployed in a solution of previously filtered water and the particles shed are counted by one of several available particle-counting instruments. Example instruments would be those that work by light scattering, instruments that work by light obscuration, such as the Hiac-Royco, or the Coulter counter which works by electrical conductivity. Elevated numbers, and sizes, of particles shed are indicative of coating failure, which is affected by crimping damage either in the form of coating pieces that are completely shorn off, or cracks in the coating which propagated during stent expansion to liberate particles. Yet another approach to measuring the effects of coating crimping damage is by acute thrombogenicity testing, one example of which is that detailed by Sukavaneshvar et al. ASAIO Journal, Aug. 11, 2000, p 301 and ASIAO Journal, Jul. 5, 2000, p M393, which approach subjected stents deployed in tubing to a flow of bovine blood in which the platelets have been radiolabeled. Accumulation of platelets and thrombus is a measure of the acute thrombogenicity. The effect of coating cracks and defect can be compared to uncoated stents, or to stents where the coatings have fewer, or no cracks and coating defects.

While particular embodiments of the invention have been shown and described, it will be obvious to those skilled in the art that changes and modifications can be made without departing from this invention in its broader aspects and, therefore, the appended claims are to encompass within their scope all such changes and modifications as fall within the true spirit and scope of the invention.

What is claimed is:

1. A method of producing a stent-balloon assembly, comprising:
    (a) providing a stent having a polymeric component;
    (b) exposing the stent to a relative humidity of 20% to 100% (RH); and
    (c) crimping the stent on a balloon of a catheter assembly.

2. The method of claim 1, wherein the relative humidity is higher than the relative humidity maintained at a cleaning room in which the stent is crimped.

3. The method of claim 1, wherein the relative humidity is 50% to 100%.

4. The method of claim 1, wherein the relative humidity is 75% to 100%.

5. The method of claim 1, wherein the duration of exposure to humidity is long enough for the polymeric component to absorb moisture so as to lower the glass transition temperature of the polymeric component by about 10%, the temperature measurement being in ° C.

6. The method of claim 1, wherein the polymeric component has a glass transition temperature greater than 60° C. in a dry state.

7. The method of claim 1, wherein the polymeric component has a glass transition temperature greater than 90° C. in a dry state.

8. The method of claim 1, wherein the polymeric component is a phosphoryl choline acrylate polymer.

9. The method of claim 1, wherein the polymeric component is included in a coating on the stent.

10. The method of claim 1, wherein a body of the stent is made at least in part from the polymeric component.

11. The method of claim 1, wherein the exposing to humidity is performed in a humidity chamber prior to crimping of the stent on the balloon.

12. The method of claim 1, wherein the exposing to humidity is performed during the crimping of the stent on the balloon wherein the stent is disposed in a crimping apparatus.

13. The method of claim 12, wherein the crimping apparatus comprises:
  (a) a work space in which the stent is placed for application of a force to the stent; and
  (b) means for introducing moisture into the workspace for increasing the humidity of the workspace.

14. The method of claim 1, wherein the polymeric component includes a drug.

* * * * *